(12) United States Patent
Smith et al.

(10) Patent No.: US 12,409,168 B2
(45) Date of Patent: Sep. 9, 2025

(54) FORMULATIONS OF AMINOPENICILLIN AND METHODS FOR SOLUBILIZING AMINOPENICILLIN

(71) Applicant: VETERINARY PHARMACY CORPORATION, St. Peter, MN (US)

(72) Inventors: Patrick John Smith, St. Peter, MN (US); Patrick Leon Soderlund, St. Peter, MN (US); William Anthony Soderlund, Jr., St. Peter, MN (US)

(73) Assignee: VETERINARY PHARMACY CORPORATION, St. Peter, MN (US)

( * ) Notice: Subject to any disclaimer, the term of this patent is extended or adjusted under 35 U.S.C. 154(b) by 0 days.

(21) Appl. No.: 18/807,584

(22) Filed: Aug. 16, 2024

(65) Prior Publication Data
US 2025/0057818 A1    Feb. 20, 2025

Related U.S. Application Data

(60) Provisional application No. 63/619,658, filed on Jan. 10, 2024, provisional application No. 63/520,220, filed on Aug. 17, 2023.

(51) Int. Cl.
| | | |
|---|---|---|
| *A61K 31/43* | (2006.01) | |
| *A61K 9/08* | (2006.01) | |
| *A61K 9/16* | (2006.01) | |
| *A61K 47/02* | (2006.01) | |
| *A61K 47/12* | (2006.01) | |
| *A61K 47/18* | (2017.01) | |
| *A61K 47/22* | (2006.01) | |

(52) U.S. Cl.
CPC .............. *A61K 31/43* (2013.01); *A61K 9/08* (2013.01); *A61K 9/1611* (2013.01); *A61K 9/1617* (2013.01); *A61K 47/02* (2013.01); *A61K 47/12* (2013.01); *A61K 47/183* (2013.01); *A61K 47/22* (2013.01)

(58) Field of Classification Search
CPC ........ A61K 31/43; A61K 9/08; A61K 9/1611; A61K 9/1617; A61K 47/02; A61K 47/12; A61K 47/183; A61K 47/22
See application file for complete search history.

(56) References Cited

U.S. PATENT DOCUMENTS

| | | | |
|---|---|---|---|
| 3,969,524 A * | 7/1976 | Emodi | A61K 31/43 514/197 |
| 5,801,153 A | 9/1998 | Badaway | |
| 2005/0136117 A1 | 6/2005 | Ramsey et al. | |
| 2010/0035856 A1 * | 2/2010 | Mertin | A23K 50/10 514/192 |
| 2018/0243333 A1 | 8/2018 | Brown et al. | |

FOREIGN PATENT DOCUMENTS

| | | | |
|---|---|---|---|
| CN | 102961381 A * | 3/2013 | |
| CN | 108261397 A | 7/2018 | |
| CN | 111529493 A * | 8/2020 | |
| KR | 101898282 B1 | 9/2018 | |

OTHER PUBLICATIONS

ReAgent, What is Sterile Water, 2022. (Year: 2022).*

* cited by examiner

*Primary Examiner* — James H Alstrum-Acevedo
*Assistant Examiner* — Manahil Mirghani Ali Abdalhameed
(74) *Attorney, Agent, or Firm* — Greenberg Traurig, LLP

(57) ABSTRACT

A formulation of a single phase solution, including aminopenicillin, a stabilizing agent, and water. The aminopenicillin in the solution has a potency of 87% or higher at 24 hours of storage at room temperature. A formulation of a single phase solution, including amoxicillin, ampicillin, and/or a combination thereof, a stabilizing agent, and water. The amoxicillin, ampicillin, and/or a combination thereof in the solution has a potency of 87% or higher at 24 hours of storage at room temperature. A formulation of a single phase solution, including amoxicillin, a stabilizing agent, and water. The amoxicillin in the solution has a potency of 87% or higher at 24 hours of storage at room temperature. A formulation of a single phase solution, including ampicillin, a stabilizing agent, and water.

16 Claims, No Drawings

FORMULATIONS OF AMINOPENICILLIN AND METHODS FOR SOLUBILIZING AMINOPENICILLIN

CROSS-REFERENCE TO RELATED APPLICATIONS

This application claims priority to U.S. provisional patent application Ser. No. 63/520,220, filed on Aug. 17, 2023; and U.S. provisional patent application Ser. No. 63/619,658, filed on Jan. 10, 2024; both applications are herein incorporated by reference in their entirety.

FIELD

The present disclosure relates generally to formulating a compound to be in a soluble form for treatment of animals.

BACKGROUND

Amoxicillin is an effective antibiotic which is widely use. Amoxicillin holds significant importance in modern medicine. Its importance lies in its effectiveness against a broad range of bacterial infections and its relative low toxicity. Amoxicillin is classified as a broad-spectrum antibiotic. Amoxicillin has been used to treat a range of infections, including respiratory tract infections (such as pneumonia, bronchitis, and sinusitis), ear infections, urinary tract infections, skin infections, and other infections.

SUMMARY

Following summary is a high-level overview of various aspects and introduces some of the concepts that are further described in the Detailed Description section. This summary is not to be used in isolation to determine the scope of the claimed subject matter. The subject matter should be understood by reference to appropriate portions of the entire specification, any or all drawings, and each of the claims.

In some aspects, the techniques described herein relate to a composition including a single phase solution. According to some embodiments, the single phase solution is a clear solution, or substantially clear solution. According to some embodiments, the single phase solution includes an aminopenicillin (e.g., amoxicillin, ampicillin, and/or a combination thereof); a stabilizing agent; and water, wherein the aminopenicillin has a high potency at 24 hours. The term "high potency" can be a potency at or above 73%, according to some embodiments. The term "high potency" can be a potency at or above 75%, according to some embodiments. The term "high potency" can be a potency at or above 80%, according to some embodiments. The term "high potency" can be a potency at or above 84%, according to some embodiments. The term "high potency" can be a potency at or above 85%, according to some embodiments. The term "high potency" can be a potency at or above 87%, according to some embodiments. The term "high potency" can be a potency at or above 89%, according to some embodiments. The term "high potency" can be a potency at or above 90%, according to some embodiments. The term "high potency" can be a potency at or above 97%, according to some embodiments.

In some aspects, the techniques described herein relate to a composition, wherein the stabilizing agent includes: a salt(s) and/or ester(s) of sorbic acid (e.g., with metal element cations, such as for example, calcium, sodium, etc.). As alternative to the salt(s) and/or ester(s) of sorbic acid, in some aspects, salts of butyric acid, propionic acid, and/or combination(s) thereof could be used (e.g., with metal element cations, such as for example, calcium, sodium, etc.).

In some aspects, the stabilizing agent includes, at least, ethyl sorbate.

In some aspects, the techniques described herein relate to a composition, wherein the stabilizing agent includes a potassium sorbate, a potassium carbonate, or a combination thereof.

In some aspects, the techniques described herein relate to a composition, wherein the stabilizing agent includes a salt of maleic acid.

In some aspects, the techniques described herein relate to a composition, wherein the stabilizing agent further includes a salt(s) and/or ester(s) of sorbic acid.

In some aspects, the techniques described herein relate to a composition, wherein the stabilizing agent includes a disodium maleate.

In some aspects, the techniques described herein relate to a composition, wherein the stabilizing agent further includes a salt(s) and/or ester(s) of sorbic acid.

In some aspects, the techniques described herein relate to a composition, wherein the aminopenicillin has a high potency at 24 hours.

In some aspects, the techniques described herein relate to a formulation including: an aminopenicillin, wherein the aminopenicillin is in a powder form; a stabilizing agent, wherein the stabilizing agent is in a powder form, wherein a mass ratio of the stabilizing agent to the aminopenicillin is at least 0.03:1 Amoxicillin Activity. In some aspects, the mass ratio of the stabilizing agent to the aminopenicillin is at least 2:1. In some aspects, the mass ratio of the stabilizing agent to the aminopenicillin is about 2:1, about 4:1, about 6:1, or about 6.13:1.

In some aspects, the techniques described herein relate to a formulation, wherein the stabilizing agent includes a salt(s) and/or ester(s) of sorbic acid.

In some aspects, the techniques described herein relate to a formulation, wherein the stabilizing agent includes a potassium sorbate, a potassium carbonate, or a combination thereof.

In some aspects, the techniques described herein relate to a formulation, wherein the stabilizing agent includes a salt(s) and/or ester(s) of sorbic acid.

In some aspects, the techniques described herein relate to a formulation, wherein the stabilizing agent includes a disodium maleate.

In some aspects, the techniques described herein relate to a method for preparing a single phase solution, wherein the method includes: obtaining a mixture, wherein the mixture includes an aminopenicillin, and a stabilizing agent; obtaining a water; combining the mixture and the water to dissolve the mixture in the water, wherein after 24 hours at room temperature, a potency of the aminopenicillin is a high potency.

In some aspects, the techniques described herein relate to a method, wherein after 24 hours at room temperature, the potency of the aminopenicillin is a high potency.

In some aspects, the techniques described herein relate to a method, wherein after 24 hours at room temperature, the potency of the aminopenicillin is from 90% to 97%.

In some aspects, the techniques described herein relate to a method, wherein the pH of the single phase solution is from 7.4 to 7.8.

In some aspects, the techniques described herein relate to a method, wherein the stabilizing agent includes a salt(s) and/or ester(s) of sorbic acid.

In some aspects, the techniques described herein relate to a method, wherein the stabilizing agent includes a potassium sorbate, a potassium carbonate, or a combination thereof.

In some aspects, the techniques described herein relate to a method, wherein the stabilizing agent includes a salt of maleic acid.

In some aspects, the techniques described herein relate to a method, wherein the stabilizing agent includes a salt(s) and/or ester(s) of sorbic acid.

In some aspects, the techniques described herein relate to a method, wherein the stabilizing agent includes a potassium sorbate.

DETAILED DESCRIPTION

Aminopenicillin as used herein includes Amoxicillin, Ampicillin, and/or a combination thereof. The embodiments disclosed here in may have application to animals, mammals, etc. The embodiments disclosed herein are directed towards treatment(s) of animals, mammals, and even humans. The various treatments can include, according to some embodiments, bacterial infections.

The embodiments and examples discussed herein are directed towards manufacturing of a concentrated medicated stock solution containing Aminopenicillin. This stock solution can then be metered out at a specific dose for all day delivery of the medication (i.e., Aminopenicillin) for either a single animal or entire herd of animals. For example, the embodiments and examples herein are directed towards making concentrated stock solution(s) of Aminopenicillin which is then metered out at, for example, 1:128 dilution factor. The embodiments of the stock solution can be made either from a pre concentrated blend of Aminopenicillin and stabilizers or where Aminopenicillin is added first to the solution followed shortly by the stabilizer component. The blend of some components can either be in powder or liquid form.

According to some embodiments, Amoxicillin is used, which is a beta-lactam (β-lactam) antibiotic that has impressive coverage over many organisms that affect swine and other animals in the veterinary industry. One of the major issues seen with Amoxicillin is its poor water solubility. Its Solubility in the trihydrate salt form is estimated between 0.095 mg/ml and 3.4 mg/ml depending on the source assessed. Generally, it is prepared as either a suspension or injectable solution to be administered in a 24 hour period. As a time-dependent antibiotic, it is imperative to maintain a specific concentration over a given range when fresh product is delivered.

Further, the quality of water which can be found in the field can vary substantially. Accordingly, it is generally understood that "water" used in solubility tests are purified water, distilled water, or high quality water with extremely low amounts of contaminants (e.g., what is generally known as "hard water" is not or cannot be used). In contrast, some of the embodiments in this disclosure have been tested with various water sourced across the United States of America. It has been determined that, according to some embodiments, the "water" can be water sources from the field, a well, or other convenient sources, where the "water" is not purified (e.g., distilled) water. These embodiments were able to still achieve a single phase solution mixture and have stable high potency at 24 hours (or longer). As such, treatment of animals (e.g., swine, etc.) in the field can be improved by the embodiments herein, as the high potency can be achieved and maintained for longer periods of time, even when convenient water sources are used.

There are three major challenges with Amoxicillin: (1) Chemical stability over time; (2) Inherently insoluble nature; and (3) Gaps in coverage that arise from resistance mechanisms of various pathogens. These three challenges are discussed in detail below.

Chemical Stability

Amoxicillin's stability in an aqueous solution can be affected by concentration of Amoxicillin, temperature, pH, time, and any combination(s) thereof. For example, Amoxicillin begins to break down (as all beta-lactams do) due to hydrolysis of the molecule. This breakdown is enhanced by factors such as pH, concentration, and/or Temperature.

For example, Amoxicillin dissolved at a concentration of 0.42 mg/ml utilizing a buffered solution at a pH of 8.04. This formulation showed degradation to 73% at 24 hours. There was no degradation at a concentration of 0.00015 mg/ml at 24 hours. This demonstrated the enhanced stability amoxicillin has at lower concentrations and slightly elevated pH.

An injectable Amoxicillin (e.g., for use with an IV pump, and formulated with excipients) is known to have increased degradation as temperature is increased, for example, from 1.92%/hour (at 5° C.) to 3.29%/hour (at 37° C.). It is generally understood that generally, Amoxicillin products is the more stable at colder temperatures.

Solubility

Generally, Amoxicillin and Ampicillin have been known to have the highest stability between a pH of 5-8. Further, generally, Amoxicillin and Ampicillin are known to be unstable outside of the pH range of 5-8. However, generally, it had been known that this pH range coincides with the lowest solubility of Amoxicillin. For example, it was generally known that in acidic environments, the Amoxicillin is extremely unstable, and has high degradation at the levels of pH of 8-9, or at higher pH.

Bacterial Resistance

Beta lactams are generally known to have problems with gram negative and other bacteria that produce resistance mechanisms that cause loss of coverage. One of the best known is beta lactamases which destroy the beta lactam ring when it enters the cell wall. As such, it was generally understood that, while Amoxicillin retains some minor gram negative coverage, without a beta-lactamase inhibitor like clavulanic acid or sulbactam, Amoxicillin is predominantly a gram positive agent.

Embodiments and Properties

According to some embodiments, formulations of Aminopenicillin in solution includes potassium sorbate (or other salts or chemically similar structures). According to some embodiments, formulations of Amoxicillin in solution includes potassium sorbate (or other salts or chemically similar structures). Potassium sorbate can be effective against gram negative bacteria.

According to some embodiments, formulations of Aminopenicillin in solution includes potassium carbonate (or other salts or chemically similar structures). According to some embodiments, formulations of Amoxicillin in solution includes potassium carbonate (or other salts or chemically similar structures).

Surprisingly and unexpectedly, formulations that include Amoxicillin and potassium sorbate, when added in varying ratios, was able to solubilize the Amoxicillin at a higher than normal concentrations. Embodiments of the formulations also had surprisingly unexpected properties. According to the embodiments, the pH achieved at solubilization was at what was generally understood to be an insoluble range for normal amoxicillin solutions. For example, according to the embodiments, single phase solutions were achieved at pH of 7.5 to 7.6. Because of the lower pH of these solutions, it was theorized that the Amoxicillin according to the embodiments could lead to better stability of the product compared to other known methods of solubilization. Potency studies demonstrated that the formulations according to some embodiments had at least a 7% higher potency at 24 hours, and up to a 13-15% potency difference at 48 hours. Some embodiments of the Amoxicillin solutions maintained greater than 80% potency at 24 hours.

According to some embodiments, it was also found that potassium sorbate surprisingly and unexpectedly lowers the requirement of Alkaline base or other alkaline solubilizers by a minimum of 10× than what was generally understood to be required.

Examples of Formulations

The following are formulation examples according to the various embodiments disclosed herein. It is to be understood that the examples provided herein are not necessarily limiting. In all of the Formulations below, the powder blend(s) immediately form a single phase colloidal solution. In all of the Formulations below, Amoxicillin Powder was at 99.6% potency. It should be noted that the Amoxicillin percentage is given as the Amoxicillin base. The Amoxicillin Trihydrate form is what has been used to compound these various Formulations.

| Formulation 1: | |
| --- | --- |
| Amoxicillin Powder 1.71% (wt/vol) | 1.71 g |
| Potassium Sorbate 35.18% (wt/vol) | 35.18 g |
| Water Q.S. | 100 ml |

| Formulation 2: | |
| --- | --- |
| Amoxicillin 1.65% (wt/vol) | 1.65 g |
| Potassium Sorbate 21% (wt/vol) | 21 g |
| Niacinamide 8.4% (wt/vol) | 8.5 g |
| Water Q.S. | 100 ml |

This formulation had a hydrotrope added for attempts at further solubilization and stabilization. This formulation's pH was 7.69 and was a very stable solution. It could be concluded that a hydrotrope could or could not be part of the formulation. A hydrotrope of Niacinamide by itself was not enough to solubilize the amoxicillin in any experiments undertaken.

| Formulation 3: | |
| --- | --- |
| Amoxicillin 1.7% (wt/vol) | 1.7 g |
| Potassium Sorbate 20% (wt/vol) | 20 g |
| Niacinamide 10% (wt/vol) | 10 g |
| Water Q.S. | 100 ml |

| Formulation 4: | |
| --- | --- |
| Amoxicillin 2% (wt/vol) | 2 g |
| Potassium Sorbate 15% (wt/vol) | 15 g |

| Formulation 4: | |
| --- | --- |
| Proline 15% (wt/vol) | 15 g |
| Water Q.S. | 100 ml |

It should be noted that proline can be utilized as another hydrotrope for added solubilization to the product. It did not however improve upon stability compared to samples without it.

| Formulation 5: | |
| --- | --- |
| Amoxicillin 1.42% (wt/vol) | 1.42 g |
| Potassium Sorbate 13% (wt/vol) | 13 g |
| Niacinamide 7.2% (wt/vol) | 7.2 g |
| Water Q.S. | 100 ml |

This Formulation showed potency of 45% at 15 days when stored at room temperature. In comparison, previously known formulations of Amoxicillin was unable to be quantified after >72 hours at room temperature.

| Formulation 6: | |
| --- | --- |
| Amoxicillin 1.51% (wt/vol) | 1.51 g |
| Potassium Sorbate 25% (wt/vol) | 25 g |
| Alkaline base 0.1% (wt/vol) | 0.1 g |
| Water Q.S. | 100 ml |

This Formulation demonstrated the reduction in the required ratio of Alkaline base to Amoxicillin for solubilization. Generally, it is understood that a 0.96% solution of Alkaline base is required for solubilizing the Amoxicillin at the target 60 g/gal concentration. In this Formulation, only 0.1% solution of Alkaline base was required.

| Formulation 7: | |
| --- | --- |
| Amoxicillin 1.613% (wt/vol) | 1.613 g |
| Potassium Sorbate 21.78% (wt/vol) | 21.78 g |
| Niacinamide 7.24% (wt/vol) | 7.24 g |
| Water Q.S. | 100 ml |

According to some embodiments of methods for preparing the above Formulation, the method includes obtaining each of water (e.g., at or around room temperature), powders of Amoxicillin, potassium sorbate, and niacinamide, combining the powders with the water and rest for 24 hours. A single phase solution was obtained. The solution was tested for potency at time 24 hours and was found to have 91% potency remaining at this time. This is a significant breakthrough compared to all other known formulations (e.g., Comparative Examples below) previously tested of other types of Amoxicillin, and what is known about concentrated amoxicillin solutions at room temperature.

The above Formulation 7 was compared to a sample containing solubilized Amoxicillin and Alkaline base (having similar concentrations) was also studied (for a 48 hour potency testing). The results were surprising and unexpected. The results showed a potency of 73.37% potency (for solubilized Amoxicillin and Alkaline base) vs. 85.9% potency (for Formulation 7).

| Formulation 8: | |
| --- | --- |
| Amoxicillin 1.065% (wt/vol) | 1.065 g |
| Potassium Sorbate 18.4% (wt/vol) | 18.4 g |
| Water Q.S. | 100 ml |

This Formulation recorded a pH of 7.5

| Formulation 9: | |
| --- | --- |
| Amoxicillin 1.062% (wt/vol) | 1.062 g |
| Potassium Sorbate 17.84% (wt/vol) | 17.84 g |
| Niacinamide 3.56% (wt/vol) | 3.56 g |
| Water Q.S. | 100 ml |

Niacinamide was theorized to be able to prevent the need for greater amounts of potassium sorbate as a hydrotrope. In this case, Niacinamide slightly reduced the potassium sorbate needed.

| Formulation 10: (Surprisingly high concentration achieved) | |
| --- | --- |
| Amoxicillin 5% (wt/vol) | 5 g |
| Potassium Sorbate 57.01% (wt/vol) | 57.01 g |

This Formulation established a lower ratio of Potassium Sorbate needed to solubilize Amoxicillin then previously seen. The ratio was 11.4 g of Potassium Sorbate to 1 g of Amoxicillin Base.

| Formulation 11: (24 hour stability test) | |
| --- | --- |
| Amoxicillin 2.29% (wt/vol) | 2.29 g |
| Potassium Sorbate 22% (wt/vol) | 22 g |
| Niacinamide 7.5% (wt/vol) | 7.5 g |
| Water Q.S. | 100 ml |

Potency: 86% at 24 hours. This is surprising and unexpected as Amoxicillin is known to have a concentration dependent degradation rate. That is, it is generally understood that a lower concentration is required to increase stability. Accordingly, this Formulation having above 80% potency at 24 hours at a 1.5× concentration is surprising and unexpected. Based on generally understood information, it would have been expected to have about 66% potency at 24 hours.

| Formulation 12: (48 hour stability test) | |
| --- | --- |
| Amoxicillin 1.613% (wt/vol) | |
| Potassium Sorbate 21.78% (wt/vol) | |
| Niacinamide 7.24% (wt/vol) | |
| Water Q.S. | 100 ml |

Potency: 85.6% at 48 hours. This shows surprising and significant improved stability compared to known Amoxicillin samples stored at room temperature.

| Formulation 13: | |
| --- | --- |
| Amoxicillin 1.64% (wt/vol) | 1.64 g |
| Potassium Sorbate 35.18% (wt/vol) | 35.18 g |
| Water Q.S. | 100 ml |

| Formulation 14: | |
| --- | --- |
| Amoxicillin 1.64% (wt/vol) | 1.64 g |
| Potassium Sorbate 27.27% (wt/vol) | 27.27 g |
| Water Q.S. | 100 ml |

This formulation achieved a surprising and unexpected breakthrough in stability of the Amoxicillin at 24 hours. Testing conducted showed the product remained at 97% potency at 24 hours. Some examples showed at least 91% potency at 24 hours. Accordingly, some embodiments have a potency range of from 91% to 97% potency at 24 hours. Accordingly, some embodiments have at least 90% potency at 24 hours.

| Formulation 15: | |
| --- | --- |
| Amoxicillin 1.61% (wt/vol) | 1.61 g |
| Potassium Sorbate 20.65% (wt/vol) | 20.65 g |
| Niacinamide 8.22% (wt/vol) | 8.22 g |
| Water Q.S. | 100 ml |

This Formulation showed 94% potency at 24 hours. Less Potassium Sorbate was necessary in the solubilization process.

| Formulation 16: | |
| --- | --- |
| Amoxicillin 1.63% (wt/vol) | 1.63 g |
| Potassium Sorbate 21.21% (wt/vol) | 21.21 g |
| Urea 12.45% (wt/vol) | 12.45 g |
| Water Q.S. | 100 ml |

| Formulation 17: | |
| --- | --- |
| Amoxicillin (1.58% wt/vol) | 0.79 g |
| Potassium Sorbate 0% (wt/vol) | 0 g (None) |
| Alkaline base (0.82% wt/vol) | 0.408 g |
| Sodium Propionate (11.2074%) | 5.6037 g |
| Water Q.S. | 50 ml |

This Formulation did not include Potassium Sorbate. Instead, Sodium Propionate was included. This Formulation had 74.9% (or about 75%) potency at 24 hours, and showed some signs of structure breakdown during chromatography. It is believed that Sodium Propionate might provide some stability enhancement while decreasing the amount of Alkaline base needed. Sodium Propionate did show some benefit as a solubilizer, but did not achieve anywhere near the potency over time of some of the other Formulations.

| Formulation 18: | |
| --- | --- |
| Amoxicillin 1.634% (wt/vol) | 0.817 g |
| Potassium Sorbate 10.0138% (wt/vol) | 5.0069 g |
| Alkaline base 0.609% (wt/vol) | 0.3046 g |
| Water Q.S. | 50 ml |

This Formulation surprisingly and unexpectedly showed that reduced amounts of Alkaline base and Potassium Sorbate are required when combined together, as compared to using each separately. This Formulation retained a potency of 93% at 24 hours. One of the benefits of this Formulation is a reduction in the ratio of Potassium Sorbate to Amoxicillin (the ratio being 6.13:1). This Formulation also reduced the required amount of Alkaline base by 36%.

| Formulation 19: | |
|---|---|
| Amoxicillin 1.81% (wt/vol) | 0.9034 g |
| Potassium Sorbate 0% (wt/vol) | 0 g (None) |
| Proline 3.0462% (wt/vol) | 1.5231 g |
| Alkaline base 1.1412% (wt/vol) | 0.5706 g |
| Water Q.S. | 50 ml |

This Formulation did not include Potassium Sorbate. Adding a second amino acid to the amino acid Alkaline base might provide increased stability. However, when Proline was added, Amoxicillin potency of 63.05% was seen at 24 hours with signs of significant breakdown. Another experiment using the amino acid Taurine was performed, and that formulation had a potency of <25% at 24 hours. It was therefore concluded that this is a sign of incompatibility for long term stability of Amoxicillin.

The Formulations discussed above exemplify how utilizing Potassium Sorbate was able to create extremely stable compounds of Amoxicillin in aqueous solutions. At least one advantageous application(s) of the formulations herein is the ability to mix with other agents to lower the amount of Potassium Sorbate in the formulation but achieving at least 87% potency of Amoxicillin at 24 hours. Further, at least one advantageous application(s) of the formulations herein is the ability to mix with other agents to lower the amount of Potassium Sorbate in the formulation but achieving a greater than 90% potency of Amoxicillin at 24 hours.

While some experiments can be conducted using pure powder forms of Amoxicillin, the following Formulations 20 and 21 utilize Amoxicillin powder derived from capsule materials in a pharmacy compounding process. According to embodiments of the compounding process, the process includes obtaining Amoxicillin capsules; obtaining ground materials by grounding the Amoxicillin capsules; sifting the ground materials to remove as much excess capsule material as possible; and then obtaining powdered Amoxicillin from the sifting. The powder is then tested via HPLC assay to assess potency of Amoxicillin base to help with adding correct amount of powder to desired stock solution concentration. There was a concern with this process that some capsule fragments would still remain and not be dissolved in water. Generally, it was expected that these capsule fragments would settle to the bottom of the stock solution, and could be problematic for water medicator systems. Surprisingly and unexpectedly, it was found that utilizing potassium sorbate with the compounded product resulted in a dissolution of the capsule fragments without altering the stability of the product.

| Formulation 20: (using capsulized Amoxicillin) | |
|---|---|
| Amoxicillin 1.6% (wt/vol) | 4 g |
| Potassium Sorbate 9.67% (wt/vol) | 24.1683 g |
| Alkaline base 0.57% (wt/vol) | 1.4266 g |
| Water Q.S. | 250 ml |

This Formulation has a ratio of Potassium Sorbate to Amoxicillin of 6:1. Potency of this Formulation was 92.22% at 24.5 hours.

| Formulation 21: (using capsulized Amoxicillin) | |
|---|---|
| Amoxicillin 1.6% (wt/vol) | 4 g |
| Potassium Sorbate 9.67% (wt/vol) | 24.1680 g |
| NaOH 1M (0.8%) | 2 g |
| Water Q.S. | 250 ml |

This Formulation was studied to assess how Amoxicillin would behave in the environment with a strong base used in place of Alkaline base or another basic chemical. This product tested out at 85% at 24.5 hours. This confirms that Amoxicillin is susceptible to damage in the present of strong bases (and likely acids as well). However, the inclusion of Potassium Sorbate still allowed this Formulation to beat the 24+ stability of other generally known Amoxicillin products.

As examples, the following Formulations (Formulations 22, 23, 24, 25, and 26) use one or more agent(s) that can be added in the presence of or without Potassium Sorbate to improve stability of the Amoxicillin molecule.

| Formulation 22: | |
|---|---|
| Amoxicillin 1.63% (wt/vol) | 3.26 g |
| Potassium Sorbate 2% (wt/vol) | 4 g |
| Alkaline base 0.76% (wt/vol) | 1.52 g |
| Sodium Propionate 3.1% (wt/vol) | 6.2 g |
| Water Q.S. | 200 ml |

This Formulation tested at 87.5% potency at 24 hours. While not above 90%, it is a substantial improvement over known Amoxicillin solutions and known solubilization methods.

| Formulation 23: | |
|---|---|
| Amoxicillin 1.64% (wt/vol) | 3.27 g |
| Potassium Sorbate 2% (wt/vol) | 4 g |
| Sodium Butyrate 2% (wt/vol) | 4 g |
| Alkaline base 0.81% (wt/vol) | 1.62 g |
| Water Q.S. | 200 ml |

This Formulation tested out at 87.3% at 24 hours.

| Formulation 24: | |
|---|---|
| Amoxicillin 1.579% (wt/vol) | 1.579 g |
| Potassium Sorbate 6.43% (wt/vol) | 6.43 g |
| Alkaline base 0.73% (wt/vol) | 0.73 g |
| Water Q.S. | 100 ml |

This Formulation used a Potassium Sorbate to Amoxicillin ratio of 4:1. Surprisingly and unexpectedly, the potency at 24.5 hours was found to be 91.83%. This Formulation demonstrated that it is possible to lower the Potassium Sorbate to Amoxicillin ratio without going below a 90% potency at 24 hours.

| Formulation 25: | |
|---|---|
| Amoxicillin 1.614% (wt/vol) | 1.614 g |
| Potassium Sorbate 3.22% (wt/vol) | 3.22 g |
| Disodium Maleate 1.93% (wt/vol) | 1.93 g |
| Water Q.S. | 100 ml |

This Formulation had 90.64% potency at 24.5 hours. Surprisingly and unexpectedly, this Formulation decreased the Potassium Sorbate to Amoxicillin ratio required to ~2:1, and had the potency above 90% at 24+ hours.

| Formulation 26: | |
| --- | --- |
| Amoxicillin 1.622% (wt/vol) | 1.622 g |
| Potassium Sorbate 0% (wt/vol) | 0 g (None) |
| Disodium Maleate 0.79% (wt/vol) | 0.79 g |
| Alkaline base 0.81% (wt/vol) | 0.81 g |
| Water Q.S. | 100 ml |

This Formulation did not include Potassium Sorbate. Surprisingly and unexpectedly, this Formulation (without Potassium Sorbate) achieved Amoxicillin potency to be kept above 90% at 24 hours. The potency of the Formulation was 90.38% at the 24.5 hour mark. Disodium Maleate is a stabilizer for Amoxicillin that can be utilized with or without Potassium Sorbate.

Further to the above embodiments and examples, some embodiments are directed towards formulations and processes for mixing various agents to lower the amount of Potassium Sorbate in the formulation yet achieving high potency at 24 hours. According to some embodiments, the formulation does not include Potassium Sorbate. According to some embodiments, the formulation includes Potassium Carbonate. According to some embodiments, the formulation includes Amoxicillin and a base (e.g., such as Arginine or Sodium Hydroxide, etc.) and as a stabilizer, Potassium Carbonate. According to some embodiments, a minimum ratio of Potassium Carbonate (or any other salt of carbonate or bicarbonate) is 0.03 gm Potassium Carbonate: gm Amoxicillin Activity. According to some embodiments, a minimum ratio of Arginine or Base material is 0.012 gm Base: gm of Amoxicillin activity.

The following Examples describe formulations which have improved stabilization of the Amoxicillin.

| Formulation 27: | |
| --- | --- |
| Amoxicillin Powder | 1.63 gm/100 ml |
| Potassium Carbonate | 0.49 gm/100 ml |
| Arginine | 0.18 gm/100 ml |
| Water Q.S. | 100 ml |

This example tested out to 87.9% potency at 24 hours. This demonstrates a significant improvement with Amoxicillin when combined with basic molecules such as Arginine at a 24 hour time point. It should be noted that all carbonate salts should be considered as a potential substitute for the Potassium Carbonate.

| Formulation 28: | |
| --- | --- |
| Amoxicillin Powder | 1.623 gm/100 ml |
| Potassium Carbonate | 0.96 gm/100 ml |
| Water Q.S. | 100 ml |

This example tested out at 80.5% potency at 24 hours.

| Formulation 29: | |
| --- | --- |
| Amoxicillin Powder | 1.631 gm/100 ml |
| Arginine | 0.55 gm/100 ml |

| Formulation 29: | |
| --- | --- |
| Potassium Sorbate | 5.89 gm/100 ml |
| Potassium Bicarbonate | 0.75 gm/100 ml |
| Water Q.S. | 100 ml |

This example tested out at 84.28% potency at 24 hours and looked at utilizing a combination of Sodium Bicarbonate and Potassium Sorbate with a basic pH adjuster in Arginine to see if it improved potency of Amoxicillin. This demonstrates that Bicarbonate could theoretically be used as another stabilizer.

Additionally, the following formulations and processes summarize improved stability over comparative examples.

| Formulation 30: | |
| --- | --- |
| Amoxicillin Powder | 30 gm |
| Potassium Carbonate | 9.0 gm |
| Arginine | 3.49 gm |
| Water Q.S. | 3785 ml |

This example tested out at 96.47% potency at 24 hours. This demonstrates the concentration dependent nature of Amoxicillin degradation. It also shows the strong stability component of the stabilizer when utilized in this formulation.

| Formulation 31: | |
| --- | --- |
| Amoxicillin Powder | 60 gm |
| Potassium Carbonate | 18.0 gm |
| Water Q.S. | 3785 ml |

This example tested out at 90.22% showing the first sample without Potassium Sorbate testing above 90% at a 24 hour period.

| Formulation 32: | |
| --- | --- |
| Amoxicillin Powder | 60 gm |
| Arginine | 7.11 gm |
| Potassium Carbonate | 18.0 gm |
| Water Q.S. | 3785 ml |

This sample tested out at 89.63% at 24 hours.

| Formulation 33: | |
| --- | --- |
| Amoxicillin Powder | 60 gm |
| Arginine | 14 gm |
| Potassium Carbonate | 18.4 gm |
| Water Q.S. | 3785 ml |

This example tested out at 87.67% and was an attempt to assess whether increased arginine would have any impact on potency. In this case there was no major change between that which was seen with bulk or capsule based powder.

| Formulation 34: | |
| --- | --- |
| Amoxicillin Bulk Powder | 14.31 gm |
| Potassium Sorbate | 70.08 gm |
| Potassium Carbonate | 3.74 gm |
| Arginine | 1.77 gm |
| Water Q.S. | 1000 ml |

This example was tested to see the impact of adding Potassium sorbate a previously discovered stabilizer with Potassium Carbonate. Potency tested out at 87.93% potency at 24 hours.

According to some embodiments, a minimum ratio of Potassium Carbonate (or any other salt of carbonate or bicarbonate) is 0.03 gm Potassium Carbonate: gm Amoxicillin activity.

According to some embodiments, a minimum ratio of Arginine or Base material 0.012 gm Base:gm of Amoxicillin activity.

As exemplified above, according to some embodiments of the formulations, the stability of Amoxicillin is at least 73% at 24 hours. According to some embodiments of the formulations, the stability of Amoxicillin is at least 74% at 24 hours. According to some embodiments of the formulations, the stability of Amoxicillin is at least 75% at 24 hours. According to some embodiments of the formulations, the stability of Amoxicillin is at least 80% at 24 hours. According to some embodiments of the formulations, the stability of Amoxicillin is at least 81% at 24 hours. According to some embodiments of the formulations, the stability of Amoxicillin is at least 84% at 24 hours. According to some embodiments of the formulations, the stability of Amoxicillin is at least 85% at 24 hours. According to some embodiments of the formulations, the stability of Amoxicillin is at least 87% at 24 hours. According to some embodiments of the formulations, the stability of Amoxicillin is at least 88% at 24 hours. According to some embodiments of the formulations, the stability of Amoxicillin is at least 90% at 24 hours. According to some embodiments of the formulations, the stability of Amoxicillin is at least 96% at 24 hours.

As exemplified above, according to some embodiments of the formulations, the stability of Amoxicillin is greater than 73% at 24 hours. According to some embodiments of the formulations, the stability of Amoxicillin is greater than 74% at 24 hours. According to some embodiments of the formulations, the stability of Amoxicillin is greater than 75% at 24 hours. According to some embodiments of the formulations, the stability of Amoxicillin is greater than 80% at 24 hours. According to some embodiments of the formulations, the stability of Amoxicillin is greater than 81% at 24 hours. According to some embodiments of the formulations, the stability of Amoxicillin is greater than 84% at 24 hours. According to some embodiments of the formulations, the stability of Amoxicillin is greater than 85% at 24 hours. According to some embodiments of the formulations, the stability of Amoxicillin is greater than 87% at 24 hours. According to some embodiments of the formulations, the stability of Amoxicillin is greater than 88% at 24 hours. According to some embodiments of the formulations, the stability of Amoxicillin is greater than 90% at 24 hours. According to some embodiments of the formulations, the stability of Amoxicillin is greater than 96% at 24 hours.

Comparative Examples

The following is a comparative formulations of Amoxicillin from which the advantages and surprisingly unexpected results of the various embodiments and examples provided herein can be better understood.

Comparative Example a (Amoxicillin-Citric Acid)

| | |
| --- | --- |
| Amoxicillin | 1.585% (wt/vol) |

Citric Acid 6:1 Amoxicillin
Water Q.S. to necessary volume

Example: 1 Gallon Stock Solution

| | |
| --- | --- |
| Amoxicillin | 60 g |
| Citric Acid | 360 g |
| Water Q.S. | 3785 ml |

Stability: testing has shown comparative formulation to have ~55% potency at 24 hours, and ~20% potency at 48 hours.

Comparative Example B

| | |
| --- | --- |
| Amoxicillin | 10 gm |
| Potassium Sorbate | 114.00 gm |
| Water Q.S. | 100 ml |

This Comparative Example did not go into solution. That is, certain combination of Amoxicillin in the presence of Potassium Sorbate does not produce a single phase solution.

Aspects

The following Aspects provide exemplary embodiments. It is to be understood at any of the Aspects and/or any element of any of the Aspects can be combined with any of the other Aspects and/or any other element of any of the Aspects.

Aspect 1. A composition comprising:
  a single phase solution, including:
    an aminopenicillin (for example, amoxicillin, ampicillin, and/or a combination thereof);
    a stabilizing agent; and
    a water,
    wherein the aminopenicillin has a potency of 73% or higher at 24 hours.

Aspect 2. The composition of Aspect 1, wherein the stabilizing agent comprises:
  a salt(s) and/or an ester(s) of sorbic acid.

Aspect 3. The composition of Aspect 1, wherein the stabilizing agent comprises: a potassium sorbate, a potassium carbonate, or a combination thereof.

Aspect 4. The composition of Aspect 1, wherein the stabilizing agent comprises:
  a salt of maleic acid.

Aspect 5. The composition of Aspect 4, wherein the stabilizing agent further comprises:
  a salt(s) and/or an ester(s) of sorbic acid.

Aspect 6. The composition of Aspect 4, wherein the stabilizing agent further comprises:
  a potassium sorbate, a potassium carbonate, or a combination thereof.

Aspect 7. The composition of Aspect 1, wherein the stabilizing agent comprises:
a disodium maleate.

Aspect 8. The composition of Aspect 7, wherein the stabilizing agent further comprises:
a salt(s) and/or an ester(s) of sorbic acid.

Aspect 9. The composition of Aspect 7, wherein the stabilizing agent further comprises:
a potassium sorbate, a potassium carbonate, or a combination thereof.

Aspect 10. The composition of Aspect 1, wherein the aminopenicillin has a potency of 85% or higher at 24 hours.

Aspect 11. A formulation comprising:
an aminopenicillin, wherein the aminopenicillin is in a powder form; and
a stabilizing agent, wherein the stabilizing agent is in a powder form, wherein a mass ratio of the stabilizing agent to the aminopenicillin is about 2:1, about 4:1, about 6:1, or about 6.13:1.

Aspect 12. The formulation of Aspect 11, wherein the stabilizing agent comprises:
a salt(s) and/or an ester(s) of sorbic acid.

Aspect 13. The formulation of Aspect 11, wherein the stabilizing agent comprises:
a potassium sorbate, a potassium carbonate, or a combination thereof.

Aspect 14. The formulation of Aspect 11, wherein the stabilizing agent comprises:
a salt of maleic acid.

Aspect 15. The formulation of Aspect 14, wherein the stabilizing agent further comprises:
a salt(s) and/or an ester(s) of sorbic acid.

Aspect 16. The formulation of Aspect 14, wherein the stabilizing agent further comprises:
a potassium sorbate, a potassium carbonate, or a combination thereof.

Aspect 17. The formulation of Aspect 11, wherein the stabilizing agent comprises:
a disodium maleate.

Aspect 18. The formulation of Aspect 17, wherein the stabilizing agent further comprises:
a salt(s) and/or an ester(s) of sorbic acid.

Aspect 19. The formulation of Aspect 17, wherein the stabilizing agent further comprises:
a potassium sorbate, a potassium carbonate, or a combination thereof.

Aspect 20. A method for preparing a single phase solution, the method comprising:
obtaining a mixture,
wherein the mixture comprises:
an aminopenicillin, and
a stabilizing agent;
obtaining a water; and
combining the mixture and the water to dissolve the mixture in the water, wherein after 24 hours at room temperature, a potency of the aminopenicillin is at least 73%.

Aspect 21. The method of Aspect 20, wherein after 24 hours at room temperature, the potency of the aminopenicillin in the single phase solution is at least 85%.

Aspect 22. The method of Aspect 20, wherein after 24 hours at room temperature, the potency of the aminopenicillin in the single phase solution is at least 90%, or at least 97%.

Aspect 23. The method of Aspect 20, wherein the pH of the single phase solution is from 7.4 to 7.8.

Aspect 24. The method of Aspect 20, wherein the stabilizing agent comprises:
a salt(s) and/or an ester(s) of sorbic acid.

Aspect 25. The method of Aspect 20, wherein the stabilizing agent comprises:
a potassium sorbate, a potassium carbonate, or a combination thereof.

Aspect 26. The method of Aspect 25, wherein the stabilizing agent comprises: a salt of maleic acid.

Aspect 27. The method of Aspect 25, wherein the stabilizing agent comprises:
a salt(s) and/or an ester(s) of sorbic acid.

Aspect 28. The method of Aspect 20, wherein the stabilizing agent comprises:
a potassium sorbate, a potassium carbonate, or a combination thereof.

Aspect 29. The method of Aspect 20, wherein the stabilizing agent comprises:
a disodium maleate.

Aspect 30. The method of Aspect 29, wherein the stabilizing agent comprises:
a salt(s) and/or an ester(s) of sorbic acid.

Aspect 31. The method of Aspect 29, wherein the stabilizing agent comprises:
a potassium sorbate, a potassium carbonate, or a combination thereof.

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

The terminology used herein is intended to describe embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components. As used herein, the term "based on" is not exclusive and allows for being based on additional factors not described, unless the context clearly dictates otherwise. In addition, the meaning of "in" includes "in" and "on."

It is to be understood that changes may be made in detail, especially in matters of the construction materials employed and the shape, size, and arrangement of parts without departing from the scope of the present disclosure. This Specification and the embodiments described are examples, with the true scope and spirit of the disclosure being indicated by the claims that follow.

What is claimed is:
1. A drinkable veterinary composition for ingestion by farm animals, comprising:
a single phase solution which does not include urea, wherein the single phase solution comprises:
an aminopenicillin;
a stabilizing agent,
wherein the stabilizing agent has hydrotropic properties, wherein the stabilizing agent comprises:
a salt(s) and/or ester(s) of sorbic acid; and
a water,
wherein the water is not purified water,
wherein the aminopenicillin has a potency of 73% or higher at 24 hours.

2. The composition of claim 1, wherein the stabilizing agent comprises:
a potassium sorbate.

3. The composition of claim 1, wherein the stabilizing agent comprises:
a potassium carbonate.

4. The composition of claim 1, wherein the stabilizing agent comprises:
a salt of maleic acid.

5. The composition of claim 1, wherein the aminopenicillin has a potency of 85% or higher at 24 hours.

6. A drinkable veterinary formulation for ingestion by farm animals, comprising:
an aminopenicillin, wherein the aminopenicillin is in a powder form; and
a stabilizing agent,
wherein the stabilizing agent has hydrotropic properties,
wherein the stabilizing agent is in a powder form,
wherein a mass ratio of the stabilizing agent to the aminopenicillin is at least 0.03:1 Amoxicillin activity,
wherein the stabilizing agent comprises a salt(s) and/or ester(s) of sorbic acid,
wherein the veterinary formulation does not include urea.

7. The formulation of claim 6, wherein the stabilizing agent comprises:
a potassium sorbate, a potassium carbonate, or a combination thereof.

8. The formulation of claim 6, wherein the stabilizing agent comprises:
a potassium carbonate.

9. The formulation of claim 6, wherein the stabilizing agent comprises:
a salt of maleic acid.

10. A method for preparing a single phase drinkable veterinary solution, wherein the single phase solution is for ingestion by farm animals, the method comprising:
obtaining a mixture,
wherein the mixture does not include urea;
wherein the mixture comprises:
an aminopenicillin, and
a stabilizing agent,
wherein the stabilizing agent has hydrotropic properties,
wherein the stabilizing agent comprises a salt(s) and/or ester(s) of sorbic acid;
obtaining a water,
wherein the water is not purified water; and
combining the mixture and the water to dissolve the mixture in the water,
wherein after 24 hours at room temperature, a potency of the aminopenicillin is at least 73%.

11. The method of claim 10, wherein after 24 hours at room temperature, the potency of the aminopenicillin in the single phase solution is at least 85%.

12. The method of claim 10, wherein after 24 hours at room temperature, the potency of the aminopenicillin in the single phase solution is at least 90%.

13. The method of claim 10, wherein the pH of the single phase solution is from 7.4 to 7.8.

14. The method of claim 10, wherein the stabilizing agent comprises:
a potassium sorbate.

15. The method of claim 10, wherein the stabilizing agent comprises:
a potassium carbonate.

16. The method of claim 10, wherein the stabilizing agent comprises:
a salt of maleic acid.

* * * * *